United States Patent [19]

Hamill, Jr.

[11] 4,245,984
[45] Jan. 20, 1981

[54] ORTHODONTIC FACE BOW INNER WIRE HAVING AN INTEGRAL SAFETY EXTENSION

[76] Inventor: Maurice R. Hamill, Jr., 1127 Norwood St., Radford, Va. 24141

[21] Appl. No.: 32,869

[22] Filed: Apr. 24, 1979

[51] Int. Cl.³ ................................................. A61C 7/00
[52] U.S. Cl. ........................................................ 433/5
[58] Field of Search ............................................ 433/5

[56] References Cited

U.S. PATENT DOCUMENTS

| 3,186,089 | 6/1965 | Asher | 433/5 |
| 4,038,754 | 8/1977 | Armstrong | 433/5 |
| 4,087,915 | 5/1978 | Andrews | 433/5 |

*Primary Examiner*—Robert Peshock
*Attorney, Agent, or Firm*—Jack D. Rubenstein

[57] ABSTRACT

An orthodontic face bow is disclosed which is provided with an improved inner safety wire. The inner safety wire includes at least one end adapted for insertion into a patient-mounted buccal tube and a safety extension associated with the at least one end. The safety extension is formed integral with the inner wire, and protects the patient from accidental contact with the at least one end.

17 Claims, 8 Drawing Figures

4,245,984

1

ORTHODONTIC FACE BOW INNER WIRE HAVING AN INTEGRAL SAFETY EXTENSION

BACKGROUND OF THE INVENTION

1. Field of the Invention

This invention relates to an improved orthdontic face bow; and more particularly, to an orthodontic face bow having an inner wire which is provided with integral safety extensions projecting beyond the ends of the inner wire.

2. Description of the Prior Art

Orthodontic safety face bows are known in the prior art.

For example, *Armstrong*, U.S. Pat. No. 4,038,754 discloses a face bow having a pair of inner bow shank wires which are provided with guards adjacent the ends thereof. The guards are each comprised of a stop sleeve, a guard mounting sleeve welded to the stop sleeve and a shank wire having a loop formed at one end. The stop sleeve is positioned on the inner bow shank wire and the shank wire having the loop formed at one end is positioned within the guard mounting sleeve. The stop sleeve is secured to the inner bow shank by spot welding, soldering or crimping.

*Andrews*, U.S. Pat. No. 4,087,915 discloses a face bow having an inner wire with a pair of ends adapted for engagement with a pair of patient-mounted buccal tubes. The inner wire is provided with a pair of safety extensions for guarding the pair of ends. In one embodiment the safety extensions are each comprised of a crank-shaped wire having one portion extending beyond the inner wire end and a distal portion mounted to the inner wire apparently by soldering or welding. A pair of solder stops are provided on the inner wire for limiting entry of the inner wire ends into the buccal tubes. In another embodiment the inner wire is provided with a pair of coupling tubes adjacent each of the ends. A safety loop is provided for protecting each of the ends. The ends of the safety loops are captured within the coupling tubes. The coupling tubes are either soldered to, or left for slight movement on, the inner wire.

Thus, the *Armstrong* and *Andrews* safety face bows are of relatively complex construction each being comprised of a number of individual components which are held in place by soldering, spot welding and crimping. In practice, it has been found that the soldered, welded and crimped connections are unreliable and subject to breakage. Since exposure of the inner wire ends to contact with the user can cause grievous injury, it is most important that the safety mechanism be reliable and foolproof, thereby necessitating avoidance of unreliable solder and weld connections. Further, the use of extra components undesirably increases the weight of the face bow and makes the manufacture and assembly thereof more expensive and difficult.

SUMMARY OF THE INVENTION

An object of the present invention is to provide an improved orthodontic safety face bow.

Another object of the present invention is to provide an orthodontic face bow provided with an inner wire having an integral safety extension.

Still another object of the present invention is to provide a generally U-shaped inner wire for an orthodontic face bow having integrally formed safety extensions adjacent each of the inner wire ends for preventing accidental contact by the user therewith.

A further object of the present invention is to provide an integrally formed inner wire safety extension for an orthodontic face bow in the form of an arcuate loop which is simple and inexpensive to form and which is reliable in use and not subject to failure.

A still further object of the present invention is to provide an orthodontic face bow with an inner wire having an integrally formed safety extension in the form of a 180 degree bend.

Another object of the present invention is to provide an orthodontic face bow with an inner wire having an integrally formed safety extension in the form of a 540 degree bend.

Still another object of the present invention is to provide an orthodontic face bow with an inner wire having an integrally formed safety extension in the form of a triangle wherein a base portion of the triangle forms the safety extension portion projecting furthest beyond the inner wire ends.

A further object of the present invention is to provide an orthodontic face bow with an inner wire having an integrally formed safety extension in the form of an arcuate loop having an additional bend for both directing the inner wire ends in a rearward direction and forming an integral stop portion for limiting entry of the inner wire ends into patient-mounted buccal tubes.

A still further object of the present invention is to provide an orthodontic face bow with an inner wire having an integrally formed safety extension covered with soft plastic tubing for both increasing the effective safety extension surface area and for providing a cushioning effect.

Another object of the present invention is to provide an orthodontic face bow with an inner wire having an integrally formed safety extension in the form of an arcuate loop which provides a distal root tipping effect on the maxillary first molars and an intrusive effect on the maxillary incisors due to a helical spring winding action in the area of the arcuate loop.

More specifically, the present invention is directed to an orthodontic face bow inner safety wire comprising at least one end adapted for insertion into a patient-mounted buccal tube and at least one safety extension means associated with each said at least one end and being formed integral with said inner wire for protecting the patient from accidental contact with said at least one end.

BRIEF DESCRIPTION OF THE DRAWINGS

These and other objects and advantages will become more fully apparent as the following description is read in conjunction with the drawings wherein.

DETAILED DESCRIPTION OF THE PREFERRED EMBODIMENTS OF THE INVENTION

Figure 1:
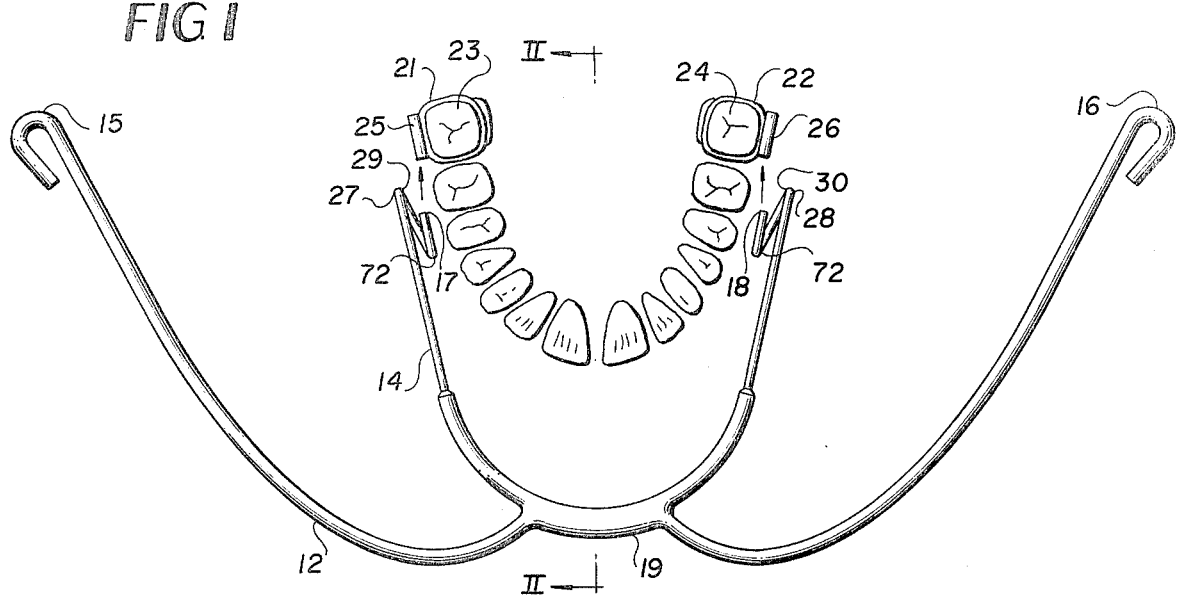
FIG. 1 is a top plan view of the improved safety face bow according to a first preferred embodiment of the invention as it would appear in actual use.

Referring now to the drawings, FIG. 1 illustrates an orthodontic face bow 10 in accordance with a first embodiment of the invention as it would appear when positioned in a patient's mouth. The face bow 10 includes an outer wire 12 and an inner wire 14 connected together at central portions 19 thereof. The outer wire 12 includes coupling loops 15 and 16 adapted for coupling the face bow 10 to a head cap and/or a neck pad through heavy rubber bands, elastic webbing or springs (not shown). The inner wire 14 includes a pair of ends 17 and 18.

The patient's mouth is provided with bands 21 and 22 surrounding upper first molars 23 and 24. The bands 21 and 22 are provided with buccal tubes 25 and 26 attached thereto. The inner wire ends 17 and 18 are adapted to be inserted into the buccal tubes 25 and 26 for applying extra-oral traction to the maxillary dental arch when the upper teeth are too far forward of the lower arch through the action of the head cap and/or neck band and the heavy rubber bands, elastic webbing or springs as applied to the outer wire 12.

The inner wire 14 is generally formed from wire having a diameter of between 0.045 and 0.050 inches. Thus, the inner wire ends 17 and 18 are sharp in the sense that they have a relatively small diameter. It has been found that the inner wire ends are capable of causing severe injuries to a patient's mouth, face and eyes if released while under tension of the heavy rubber bands, elastic webbing or springs which generally apply a force in the range of from a few ounces to several pounds.

To avoid the grievous injuries otherwise possible, the present invention contemplates the provision of safety extensions 27 and 28 projecting beyond the range of the inner wire ends 17 and 18, respectively. The safety extensions 27 and 28 are each formed integrally with the inner wire 14, and take the form of an arcuate loop.

Figure 2:
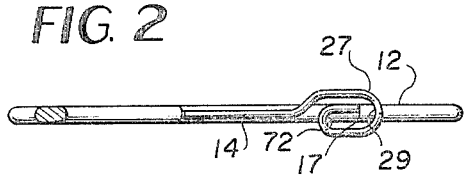
FIG. 2 is a side elevational view, in section, according to the first embodiment taken along the line II—II of FIG. 1 and removed from the patient's mouth.

In the first embodiment illustrated in FIGS. 1 and 2 the arcuate loop safety extensions 27 and 28 are formed by 180 degree bends 29 and 30, respectively.

As illustrated in FIG. 2, the inner wire ends 17 and 18 are located within the periphery of the arcuate loop safety extensions 27 and 28 thereby providing reliable protection for the patient regardless of the angle of approach in the event of an accidental release.

Figure 3:
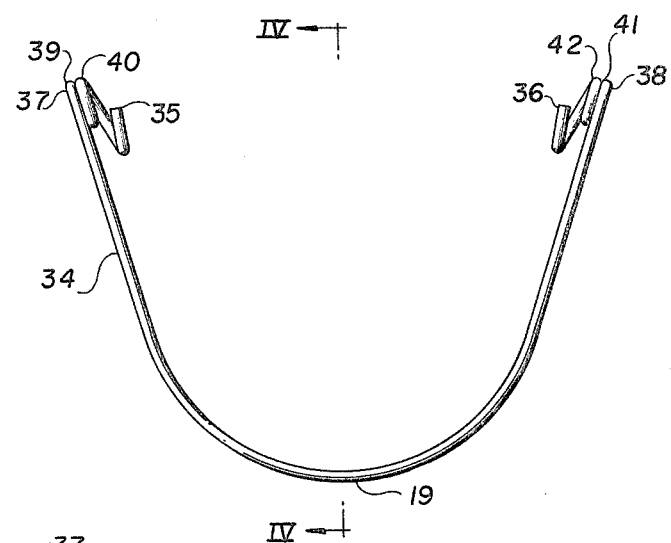
FIG. 3 is a top plan view of the improved safety inner wire according to a second preferred embodiment of the invention.
Figure 4:
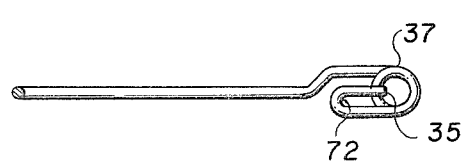
FIG. 4 is a side elevational view, in section, according to the second preferred embodiment taken along the line IV—IV of FIG. 3.

FIGS. 3 and 4 illustrate an inner wire 34 in accordance with a second embodiment of the present invention. The inner wire 34 includes a pair of safety extensions 37 and 38 projecting beyond the range of the inner wire ends 35 and 36.

The safety projections 37 and 38 are formed by a 540 degree bend which results in a leading edge 39, 40 and 41, 42 having a thickness equal to twice the diameter of the inner wire 34. This increased thickness provides a larger contact area for further reducing the likelihood of injury in the event of an accidental release.

As illustrated in FIG. 4, the inner wire ends 35 and 36 are located within the periphery of the arcuate loop safety extensions 37 and 38.

Figure 5:
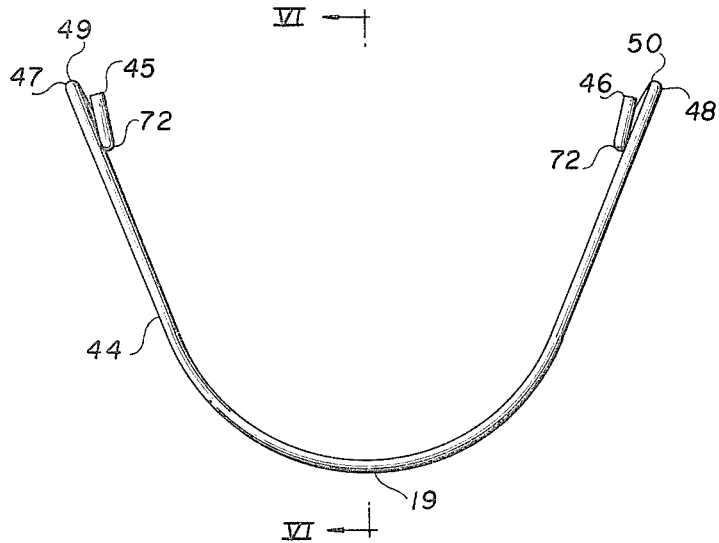
FIG. 5 is a top plan view of the improved safety inner wire according to a third preferred embodiment of the invention.
Figure 6:
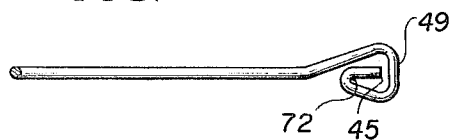
FIG. 6 is a side elevational view, in section, according to the third preferred embodiment taken along the line VI—VI of FIG. 6.

FIGS. 5 and 6 illustrate an inner wire 44 in accordance with a third embodiment of the present invention. The inner wire 34 includes a pair of ends 45 and 46 and a pair of safety extensions 47 and 48 projecting beyond the range of the inner wire ends 45 and 46.

The safety extensions 47 and 48 are formed by a plurality of arcuate bends such that a triangular shaped arcuate loop is formed. A base portion or leg 49 and 50 of the triangular shaped extensions form the rearmost portion or the portion furthest from the central portion 19.

As illustrated in FIG. 6, the inner wire ends 45 and 46 are centrally located within the periphery of the safety extensions 47 and 48.

Figure 7:
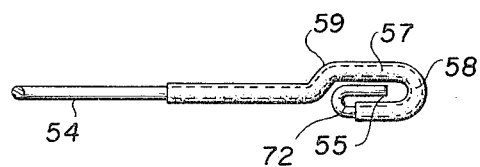
FIG. 7 is a side elevational view of one side of the improved safety inner wire according to a fourth preferred embodiment of the present invention.

FIG. 7 illustrates an inner wire 54 according to a fourth embodiment of the present invention. This embodiment is similar in appearance to the embodiment illustrated in FIGS. 1 and 2 except that the safety extension 57 is extended to provide an increased distance from the wire end 55 to the rearmost periphery 58 of the safety extension 57. Further, the safety extension is covered by a section of soft plastic tubing 59. The soft plastic tubing 59 both increases the effective surface area of the safety extension 57 and provides a cushioned impact surface.

Figure 8:
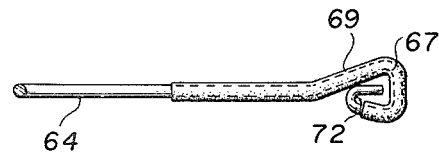
FIG. 8 is a side elevational view of one side of the improved safety inner wire according to a fifth preferred embodiment of the present invention.

FIG. 8 illustrates an inner wire 64 according to a fifth embodiment of the present invention. This embodiment is similar in appearance to the embodiment illustrated in FIGS. 5 and 6 except that the safety extension is provided with a section of plastic tubing 69 covering a safety extension 67. The soft plastic tubing 69 both increases the effective surface area of the safety extension 67 and provides a cushioned impact surface.

In each of the preferred embodiments, the inner wire is provided with an additional 180 degree bend 72 for redirecting the ends in a rearward direction or a direction away from the central portion 19. The bend can, of course, be of various other angles so long as the end extends generally parallel to the axis of the patient mounted buccal tubes when the face bow is properly mounted on the patient.

In operation, if the face bow is accidentally released during removal, the patient will be contacted by the safety extension portions which will minimize injury to the patient and reliably prevent accidental contact with the inner wire relatively sharp ends.

An added advantage of the present invention is that a distal root tipping effect on the maxillary first molars and an intrusive effect on the maxillary incisors can be accomplished when desired due to a helical spring winding action in the area of the arcuate loops. Left side elevational views in FIGS. 2, 4, 6, 7 and 8 illustrate an initial upward bend of 14 followed by a series of clockwise bends. An initial downward bend followed by a series of counterclockwise bends is used to maximize this advantage. Thus, a face bow constructed in accordance with the present invention is functionally improved in addition to being safer.

The present invention may be embodied in other specific forms without departing from the spirit or the essential characteristics thereof. The presently disclosed embodiments are, therefore, to be considered in all respects as illustrative and not restrictive, the scope of the invention being indicated by the appended claims rather than by the foregoing description and all changes which come within the meaning and range of equivalency of the claims are, therefore, to be embraced therein.

What is claimed is:

1. In an orthodontic safety face bow including a generally U-shaped inner wire and an outer wire, said inner and outer wires being coupled together at central portions thereof, said outer wire having first and second portions adapted for coupling to a head cap and/or a neck pad, and said inner wire having first and second ends adapted for insertion into patient-mounted buccal tubes, wherein the improvement comprises first and second safety extensions in the form of first and second arcuate loops, respectively, formed integral with said inner wire intermediate said first and second ends and said central portion, respectively, said safety extensions projecting beyond said first and second ends for preventing accidental contact therewith.

2. An improved orthodontic safety face bow as claimed in claim 1, wherein said first end lies within the periphery of said first arcuate loop and said second end lies within the periphery of said second arcuate loop when viewed in side elevation.

3. An improved orthodontic safety face bow as claimed in claim 1, wherein said first and second arcuate loops are formed by respective 180 degree bends in said inner wire.

4. An improved orthodontic safety bow as claimed in claim 3, wherein an additional bend is formed intermediate each said 180 degree bend and said respective first and second ends for directing said first and second ends in a direction away from said central portions, said additional bend providing an integral stop portion for limiting entry of said first and second ends into said respective buccal tubes.

5. An improved orthodontic safety face bow as claimed in claim 1, wherein said first and second arcuate loops are formed by respective 540 degree bends.

6. An improved orthodontic safety face bow as claimed in claim 5, wherein an additional bend is formed intermediate each said 540 degree bend and said respective first and second ends for directing said first and second ends a direction away from said central portions, said additional bend providing an integral stop portion for limiting entry of said first and second ends into said respective buccal tubes.

7. An improved orthodontic safety face bow as claimed in any of claims 1, 2, 3, or 4, wherein each of said first and second arcuate loops are in the form of a respective triangle, a base of each said respective triangle forming the safety extension portion projecting furthest beyond said first and second ends.

8. An improved orthondontic safety face bow as claimed in any of claims 1, 2, 3, or 4, wherein said first and second safety extensions are covered by soft plastic tubing, whereby said soft plastic tubing both increases the effective surface area and cushions said safety extensions, thereby further lessening the possibility of injury.

9. An improved orthodontic safety face bow as claimed in claim 7, wherein said first and second safety extensions are covered by soft plastic tubing, whereby said soft plastic tubing both increases the effective surface area and cushions said safety extensions, thereby further lessening the possibility of injury.

10. An inner safety wire for an orthodontic face bow comprising first and second ends adapted for insertion into patient-mounted buccal tubes, and first and second safety extensions formed integral with said inner wire, said safety extensions each comprising an arcuate loop in said inner wire extending beyond said first and second ends.

11. An inner safety wire for an orthodontic face bow as claimed in claim 10, wherein said inner wire is generally U-shaped and said first and second ends lie within the periphery of said respective arcuate loops as viewed in side elevation.

12. An inner safety wire for an orthodontic face bow as claimed in claim 10, wherein each said arcuate loop is formed by a 180 degree bend.

13. An inner safety wire for an orthodontic face bow as claimed in claim 12, wherein an addiitional bend is provided intermediate each said 180 degree bend and said respective end for redirecting each said end in a rearward direction, said additional bend providing an integral stop portion for limiting entry of each said end into said respective buccal tube.

14. An inner safety wire for an orthodontic face bow as claimed in claim 10, wherein each said arcuate loop is formed by a 540 degree bend.

15. An inner safety wire for an orthodontic face bow as claimed in claim 14, wherein an additional bend is provided intermediate each said 540 degree bend and said respective end for redirecting each said end in a rearward direction, said additional bend providing an integral stop portion for limiting entry of each said end into said respective buccal tube.

16. An inner safety wire for an orthodontic face bow as claimed in any of claims 10, 11, 12 or 13, wherein each said arcuate loop is in the form of a triangle, a base of said triangle forming the rearmost portion of each said safety extension.

17. An inner safety wire for an orthodontic face bow as claimed in claim 10, wherein said safety extensions are covered with soft plastic tubing, whereby said soft plastic tubing both increases the effective surface area and cushions said safety extensions in case of an accidental impact, thereby further lessening the possibility of injury.

* * * * *